United States Patent [19]

Sakuma et al.

[11] Patent Number: 4,691,718

[45] Date of Patent: Sep. 8, 1987

[54] TOOTHBRUSH

[75] Inventors: Shuji Sakuma; Hirotaka Fujinawa, both of Tsukiji, Japan

[73] Assignee: Kabushiki Kaisha Sangi, Tokyo, Japan

[21] Appl. No.: 846,069

[22] Filed: Mar. 31, 1986

[30] Foreign Application Priority Data

Jun. 29, 1985 [JP] Japan ................................ 60-141552

[51] Int. Cl.[4] ............................................. A61N 1/30
[52] U.S. Cl. ............................... 132/84 R; 15/159 A; 15/167 R; 128/393
[58] Field of Search ............... 15/167, 159 A; 604/20, 604/21; 132/84 A; 128/393

[56] References Cited

U.S. PATENT DOCUMENTS 2,834,344  5/1958  Kanai ................................. 128/393
3,520,297  7/1978  Bechford ........................... 132/84 R Primary Examiner—Robert Peshock
Attorney, Agent, or Firm—Stevens, Davis, Miller and Mosher

[57] ABSTRACT

A toothbrush includes a bristle portion having implanted bristles and molded from an ion eluting-type ceramic, a conductor extending into the interior of the bristle portion, and a battery to which the conductor is connected. An electric current flows from the user's hand toward the surface of the teeth through the user's body as the teeth are brushed, thereby causing calcium of fluorine ion, which elutes from the ceramic constituting the bristle portion, to be deposited onto and to penetrate the teeth and dental pulpa while tartar is removed from the surface of the teeth by electronic decomposition.

7 Claims, 2 Drawing Figures

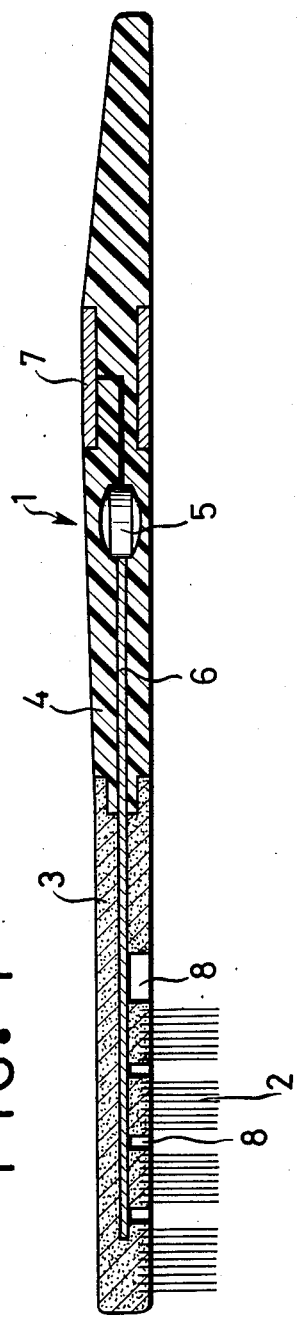
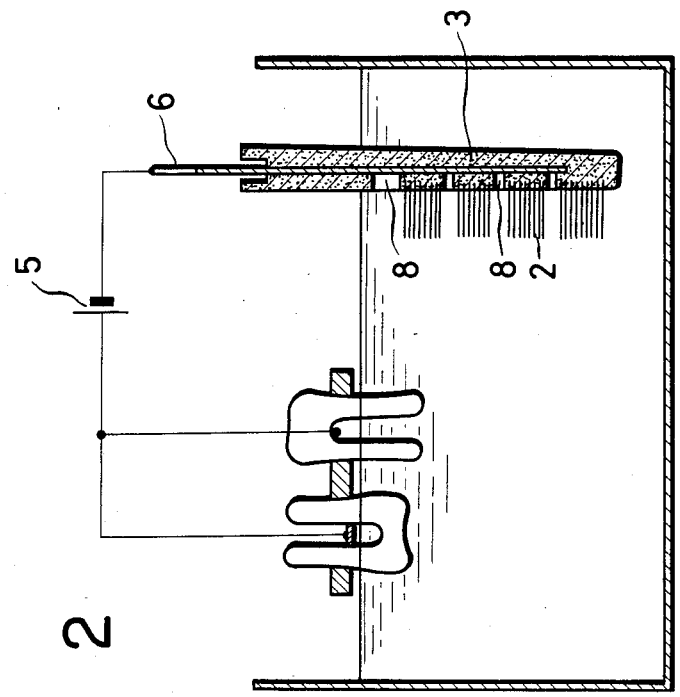

TOOTHBRUSH

BACKGROUND OF THE INVENTION

1. Field of the Invention

This invention relates to a toothbrush and, more particularly, to a toothbrush having a bristle portion molded from an ion eluting-type ceramic. The toothbrush of the present invention is effective in preventing dental caries and pyorrhea.

2. Description of the Prior Art

An ordinary toothbrush consists of a synthetic resin molded into a unitary body that includes a bristle portion having implanted hairs, hereafter referred to as bristles, and a handle portion gripped by the hand. The bristles of the toothbrush are rubbed against surfaces (corona dentis) of the user's teeth to produce friction which acts to remove tartar from the teeth. However, tartar removal requires that the toothbrush be rubbed against the teeth with considerable force. This is a drawback since such intense rubbing wears down the surfaces oi the teeth.

With the advancements that have been made in the field of minature batteries, toothbrushes incorporating such batteries have been developed and attempts have been made to utilize such toothbrushes in removing tartar from the surfaces of teeth by electronic decomposition. Toothbrushes of this kind, ordinarily referred to as electronic toothbrushes, include a battery accommodated within the handle portion, an electrically conductive rod extending to the bristle portion and having one end thereof connected to the battery, and an electrically conductive plate disposed on the surface of the handle portion and connected to the battery. When the user grasps the handle portion of the electronic toothbrush and, hence, contacts the conductive plate, an electric circuit is formed through the user's body, the user's teeth and the conductive rod. As a result, the toothbrush, which exhibits negative polarity, draws tartar of positive polarity from the surface of the teeth, thereby removing the tartar by decomposition.

Though an electronic toothbrush of this type decomposes and removes tartar from a tooth surface, absolutely no consideration is given to strengthening the tooth surface layer (cuticula dentist). In other words, a disadvantage of such an electronic toothbrush is that the tooth surface layer is inevitably worn down by contact with the bristles implanted in the bristle portion.

SUMMARY OF THE INVENTION

An object of the present invention is to provide a toothbrush capable of removing tarta from teeth by electronic decomposition when the teeth are brushed thereby.

Another object of the present invention is to provide a toothbrush capable of strengthening the surface layer of the teeth when the teeth are brushed thereby.

According to the present invention, the foregoing objects are attained by providing a toothbrush including a bristle portion having implanted bristles and molded from an ion eluting-type ceramic. Extending into the interior of the bristle portion is a conductor connected to one pole of a battery. A second conductor is connected to the pole of the battery and fixedly secured to the surface of a handle contiguous to the bristle portion. Owing to the battery, an electric current flows from the user's hand toward the surface of the teeth through the user's body as the teeth are brushed, thereby causing calcium or fluorine ions, or complexes thereof to elute from the ceramic constituting the bristle portion, to be deposited onto and to penetrate the tooth's surface and dental pulpa. The teeth and dental pulpa are thus strengthened and improved in appearance by the calcium or fluorine ion while tartar is removed from the surface of the teeth by electronic decomposition.

The preferred ion eluting-type ceramic is a molded body of an apatite ceramic such as hydroxy apatite or apatite fluoride. The bristle portion is connected to the negative pole of the battery and the second conductor on the surface of the handle portion is connected to the positive pole of the battery. The handle portion may consist of a synthetic resin material or an ion eluting-type ceramic.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a longitudinal sectional view illustrating an embodiment of a toothbrush according to the present invention, and FIG. 2 is a schematic view illustrating an experimental set-up used to test the toothbrush of the present invention.

DESCRIPTION OF THE PREFERRED EMBODIMENT

With reference first to FIG. 1, there is shown a toothbrush 1 embodying the present invention. The toothbrush 1 comprises a bristle portion 3 having implanted bristles 2, and a handle portion 4 retained by the bristle portion 3. The latter consists of an ion eluting-type ceramic, preferably a molded body of an apatite ceramic such as hydroxy apatite $[Ca_{10}(PO_4)_6(OH)_2]$ or apatite fluoride $[Ca_{10}(PO_4)_6F_2]$. The molded body of apatite ceramic may be obtained by adding 30–10 wt-% of a silicone acryl polymer or acryl resin to 70–90 wt-% of hydroxy apatite or apatite fluoride mixing the two together, applying a pressure of about 500–700 kg/cm$^2$ at room temperature and molding the mixture as in the manner of an ordinary plastic.

The handle portion 4 consists of a synthetic resin or ion eluting-type ceramic and internally accommodates a minature battery 5. Also accommodated within the handle 5 is a first conductor 6 consisting of an electrically conductive material such as silver or copper and connected at one end to the negative pole of the battery 5. The first conductor 6 extends from the battery 5 into the interior of the bristle portion 3. A second conductor 7 is disposed on the surface of the handle portion 4 and is connected to the positive pole of battery 5.

The bristle portion 3 and handle portion 4 may be molded separately and the first conductor 6 may then be inserted into the bristle portion 3 to join the bristle portion 3 and handle portion 4 into a unitary body. Alternatively, the bristle portion 3 and handle portion 4 may be integrally molded beforehand to form the unitary body and the battery may be accommodated in tbe bristle portion. Tbe bristle portion 3 is provided with a plurality oi holes 8 in the side thereof faced toward the teeth when the toothbrush is used. The holes 8 expose the first conductor 6 to the outside environment to improve its ability to conduct an electric current The holes 8 may have the form of slender slots, in which case one slot of comparatively greater length is preferably provided in the side of the bristle portion 3 adjacent the handle portion 4, as illustrated in the drawings.

In accordance with the above-described construction of toothbrush 1, the second conductor 7, which is contacted by the user's hand when the handle portion 4 is grasped, is of positive polarity owing to its connection to the positive pole of battery 5. The bristle portion 3 is of negative polarity owing to the first conductor 6 connected to the negative pole of the battery 5. Accordingly, an electric current from the battery 5 passes through the second conductor 7 and the user's hand and body and flows toward the surfaces of the teeth through dental pulpa tissue and tooth tissue. This causes calcium or fluorine ion, which elutes from the ion eluting-type ceramic constituting the bristle portion 3, to deposit on and penetrate the teeth and dental pulpa. Meanwhile, the electric current causes the organic ion of the protein substances constituting dental surface tartar to be adsorbed onto the toothbrush 1, thereby removing the tartar from the surfaces of the teeth by decomposition.

The deposition and penetration of the calcium ion or fluorine ion on and into the teeth's surface and dental pulpa are promoted during brushing if use is made of a dentifrice or solution containing calcium ion of calcium phosphate, hydroxy apatite or the like, or a dentifrice or soulution containing a fluoride.

[Experiment]

A toothbrush in accordance with the present invention was subjected to an experiment using the set-up shown in FIG. 2. The bristle portion 3, comprising hydroxy apatite $[Ca_{10}(PO_4)_6(OH)_2]$, was immersed in a salt water solution and the second conductor 6 was connected to the negative pole of the battery 5. The positive pole of battery 5 was connected to a dental pulpa cavity, and the root (radix dentis) of a tooth supported at its neck (collum dentis) via an insulator was immersed into the same salt water solution. The battery 5 had a voltage of 1.5 v. Further, the positive pole of battery 5 was connected to the dental pulpa cavity, and the tooth's surface (corona dentis) supported at its neck (collum dentis) via an insulator was immersed into the same salt water solution.

The experimental procedure consisted of brushing the surfaces of the tooth root and the tooth's surface with the bristles 2 of the experimental toothbrush six times daily everyday for one month. It was confirmed from the results that the surfaces of the tooth was coated with a layer of calcium and hydroxy apatite. It was also confirmed in a separate experiment that the surface of the tooth was coated with a layer of fluorine and apatite fluoride by using a bristle portion of apatite fluoride $[Ca_{10}(PO_4)_6F_2]$ under conditions indentical with those of the above-described experiment.

Thus, by forming at least the bristle portion of the toothbrush from an ion eluting-type ceramic, not only is dental tartar removed by decomposition, but the surfaces of the teeth are coated with a layer of calcium, fluorine, hydroxy apatite or apatite fluoride to strengthen and improve the appearance of the teeth.

As many apparently widely different embodiments of the present invention can be made without daparting from the spirit and scope thereof, it is to be understood that the invention is not limited to the specific embodiments thereof except as defined in the appended claims.

What we claim is:

1. A toothbrush comprising a bristle portion having bristles implanted therein, and a handle portion contiguous to said bristle portion, said bristle portion consisting of an ion eluting-type ceramic, said handle or bristle portion having a battery accommodated therein, a first conductor accommodated therein and connected to one pole of said battery, and a second conductor connected to the pole of said battery and fixedly secured to the surface of said handle, said iirst conductor extending into the interior of said bristle portion and exposing outward via at least one hole on said bristle portion.

2. The toothbrush according to claim 1, wherein said bristle portion comprises a molded body of an apatite ceramic.

3. The toothbrush according to claim 2, wherein said apatite ceramic is hydroxy apatite $[Ca_{10}(PO_4)_6(OH)_2]$.

4. The toothbrush according to claim 2, wherein said apatite ceramic is apatite fluoride $[Ca_{10}(PO_4)_6F_2]$.

5. The toothbrush according to claim 2, wherein said first conductor is connected to a negative pole of said battery and said second conductor is connected to a positive pole of said battery.

6. The toothbrush according to claim 5, wherein said handle portion comprises a synthetic resin material and said first conductor is insertable into said bristle portion.

7. The toothbrush according to claim 5, wherein said handle portion comprises an ion eluting-type ceramic and is integrally molded with said bristle portion.

* * * * *

UNITED STATES PATENT AND TRADEMARK OFFICE
CERTIFICATE OF CORRECTION

PATENT NO. : 4,691,718

DATED : September 8, 1987

INVENTOR(S) : Sakuma et al.

It is certified that error appears in the above-identified patent and that said Letters Patent is hereby corrected as shown below:

In the abstract, line 10, change "tartar" to read --plaque--.

Column 1, line 18, change "tartar" to read --plaque--.

Column 1, line 27, change "tartar" to read --plaque--.

Column 1, line 41, change "tartar" to read --plaque--.

Column 1, line 43, change "tartar" to read --plaque--.

Column 1, line 52, change "tarta" to read --plaque--.

Column 2, line 6, change "tartar" to read --plaque--.

Column 3, line 20, change "tartar" to read --plaque--.

Column 3, line 22, change "tartar" to read --plaque--.

Column 4, line 10, change "tartar" to read --plaque--.

Signed and Sealed this

Eighth Day of August, 1989

Attest:

DONALD J. QUIGG

*Attesting Officer*  *Commissioner of Patents and Trademarks*